(12) United States Patent
Delamarche et al.

(10) Patent No.: US 9,207,684 B2
(45) Date of Patent: Dec. 8, 2015

(54) MICROFLUIDIC SURFACE PROCESSING SYSTEMS WITH SELF-REGULATED DISTANCE-TO SURFACE CONTROL

(71) Applicant: International Business Machines Corporation, Armonk, NY (US)

(72) Inventors: Emmanuel Delamarche, Rueschlikon (CH); Martina Hitzbleck, Rueschlikon (CH); Govind Kaigala, Rueschlikon (CH); Robert Lovchik, Rueschlikon (CH)

(73) Assignee: International Business Machines Corporation, Armonk, NY (US)

(*) Notice: Subject to any disclaimer, the term of this patent is extended or adjusted under 35 U.S.C. 154(b) by 241 days.

(21) Appl. No.: 14/024,970

(22) Filed: Sep. 12, 2013

(65) Prior Publication Data
US 2014/0090715 A1  Apr. 3, 2014

(30) Foreign Application Priority Data

Sep. 28, 2012 (GB) .................................. 1217344.9

(51) Int. Cl.
*B01J 19/00* (2006.01)
*G05D 7/06* (2006.01)
*B81C 99/00* (2010.01)
(Continued)

(52) U.S. Cl.
CPC .......... *G05D 7/0694* (2013.01); *B81C 99/0025* (2013.01); *B01L 3/0293* (2013.01); *G01N 1/31* (2013.01); *G01N 1/32* (2013.01); *G01N 2035/1034* (2013.01); *Y10T 137/0318* (2015.04); *Y10T 137/8593* (2015.04)

(58) Field of Classification Search
CPC ........................... G05D 7/0694; B01L 3/0293
USPC ............................................................ 137/1
See application file for complete search history.

(56) References Cited

U.S. PATENT DOCUMENTS

| 7,870,616 B2 | 1/2011 | Meister et al. |
| 7,954,166 B2 | 5/2011 | Mirkin et al. |

(Continued)

FOREIGN PATENT DOCUMENTS

| EP | 2295096 A1 | 3/2011 |
| JP | 2003130066 A | 5/2003 |

(Continued)

OTHER PUBLICATIONS

Patent Cooperation Treaty (PCT), Search Report, International Application No. PCT/IB2013/058097, Feb. 6, 2014, 12 pages.

(Continued)

*Primary Examiner* — Cachet Sellman
(74) *Attorney, Agent, or Firm* — Cantor Colburn LLP; Gail Zarick (57) ABSTRACT

A microfluidic surface processing system includes a microfluidic probe head having a processing fluid circuit configured to dispense a surface processing fluid from a processing fluid aperture thereof; a linkage mechanism, configured to apply a force to or modulate a force applied to the microfluidic probe head towards a surface to be processed; and a lifting fluid circuit integral with the microfluidic probe head and distinct from the processing fluid circuit, the lifting fluid circuit designed for dispensing a lifting fluid from a lifting fluid aperture thereof, with pressure such as to counter the force applied or modulated by the linkage mechanism, at the level of the surface.

6 Claims, 5 Drawing Sheets

(51) Int. Cl.
*B01L 3/02* (2006.01)
*G01N 1/31* (2006.01)
*G01N 1/32* (2006.01)
*G01N 35/10* (2006.01)

(56) References Cited

U.S. PATENT DOCUMENTS

| | | | |
|---|---|---|---|
| 7,958,776 B2 | 6/2011 | Wang | |
| 2005/0063875 A1* | 3/2005 | Schatz et al. | 422/100 |
| 2005/0247673 A1 | 11/2005 | Delamarche et al. | |
| 2009/0298388 A1* | 12/2009 | Li et al. | 451/6 |
| 2009/0318786 A1 | 12/2009 | Blank et al. | |

FOREIGN PATENT DOCUMENTS

| | | |
|---|---|---|
| WO | 2006014460 A2 | 2/2006 |
| WO | 2010128483 A2 | 11/2010 |
| WO | 2012056369 A1 | 5/2012 |
| WO | WO 2012056369 A1 * | 5/2012 |

OTHER PUBLICATIONS

A. Ainla, et al. "A Microfluidic Pipette for Single-Cell Pharmacology," Anal. Chem., 82 (11), May 2010, pp. 4529-4536.

Y. Lee, et al., "Combined Scanning Electrochemical/Optical Microscopy with Shear Force and Current Feedback," Anal. Chem., 74 (15), Jun. 2002, pp. 3634-3643.

Y. Takahashi, et al., "Simultaneous Noncontact Topography and Electrochemical Imaging by SECM/SICM Featuring Ion Current Feedback Regulation," J. Am. Chem. Soc., 132 (29), Jun. 2010, pp. 10118-10126.

GB Intellectual Property Office, Application No. GB1217344.9; Patents Act 1977: Search Report Under Section 17(5); Date Mailed: Jan. 29, 2013; pp. 1-3.

* cited by examiner

MICROFLUIDIC SURFACE PROCESSING SYSTEMS WITH SELF-REGULATED DISTANCE-TO SURFACE CONTROL

PRIORITY

This application claims priority to Great Britain Patent Application No. 1217344.9, filed Sep. 28, 2012, and all the benefits accruing therefrom under 35 U.S.C. §119, the contents of which in its entirety are herein incorporated by reference.

BACKGROUND

The invention relates in general to the field of microfluidic surface processing devices and in particular to distance-to-surface control systems for such devices.

Microfluidics generally refers to microfabricated devices, which are used for moving, sampling, mixing, analyzing and dosing liquids. Prominent features thereof originate from the peculiar behavior that liquids exhibit at the micrometer length scale. Flow of liquids in microfluidics is typically laminar. Volumes well below one nanoliter can be reached by fabricating structures with lateral dimensions in the micrometer range. Reactions that are limited at large scales (by diffusion of reactants) can be accelerated. Finally, parallel streams of liquids can possibly be accurately and reproducibility controlled, allowing for chemical reactions and gradients to be made at liquid/liquid and liquid/solid interfaces. Microfluidics are accordingly used for various applications in life sciences. Many microfluidic devices have user chip interfaces and closed flowpaths. Closed flowpaths facilitate the integration of functional elements (e.g. heaters, mixers, pumps, UV detector, valves, etc.) into one device while minimizing problems related to leaks and evaporation.

Devising systems and methods for controlling and regulating the distance of microfluidic surface processing devices to the processed surface is particularly challenging: distance control in the tens and hundred of micrometer scale is required. This is even more difficult in the context of life-sciences since the surfaces are most often immersed in liquids. The surfaces may also exhibit strong variations in the topography, composition, and may not be flat even in the macroscopic world.

The known distance control systems/methods require external control systems, as well as, in some cases, pressure regulation. For example, it is known to use a beam deflection system, using a laser and photodetector to measure the beam position. A feedback loop keeps a preset amplitude constant by adjusting the piezo-length in z direction. It is, however, difficult to focus the laser in a liquid environment, and with a liquid air interface. In other, simpler approaches, an operator visually observes the sample and makes changes accordingly. In such cases the operator is the "control" system; this approach obviously suffers from a slow time response; the precision achieved is likely questionable. Still other approaches rely on a priori calibrations. Such calibrations are however specific to particular surface topographies and are time consuming. In addition, some liquid-surface interactions will not be easy, or even not possible, to visualize.

Still other approaches consist of controlling the distance of devices under liquid using current or voltage measurements with a closed-loop system. However, such approaches require a Faraday cage and are not suitable for longer distances in the tens of micrometers, as currents needed for longer distances would cause undesired heating of the system.

There is accordingly a need for simple, yet precise distance control systems and methods for microfluidic surface processing devices.

SUMMARY

In one embodiment, a microfluidic surface processing system includes a microfluidic probe head having a processing fluid circuit configured to dispense a surface processing fluid from a processing fluid aperture thereof; a linkage mechanism, configured to apply a force to or modulate a force applied to the microfluidic probe head towards a surface to be processed; and a lifting fluid circuit integral with the microfluidic probe head and distinct from the processing fluid circuit, the lifting fluid circuit designed for dispensing a lifting fluid from a lifting fluid aperture thereof, with pressure such as to counter the force applied or modulated by the linkage mechanism, at the level of the surface.

In another embodiment, method is disclosed for operating a microfluidic surface processing system having a microfluidic probe head having a processing fluid circuit configured to dispense a surface processing fluid from a processing fluid aperture thereof, a linkage mechanism, configured to apply a force to or modulate a force applied to the microfluidic probe head towards a surface to be processed, and a lifting fluid circuit integral with the microfluidic probe head and distinct from the processing fluid circuit, the lifting fluid circuit designed for dispensing a lifting fluid from a lifting fluid aperture thereof, with pressure such as to counter the force applied or modulated by the linkage mechanism, at the level of the surface. The method includes dispensing a lifting fluid via the at least one lifting fluid aperture; letting the probe head undergo the force applied by or modulated by the mechanism to approach a surface to be processed, by dropping the probe head; and processing the surface with the probe head.

BRIEF DESCRIPTION OF THE SEVERAL VIEWS OF THE DRAWINGS

FIG. 5a is a photograph of a setup for local staining of a surface with large curvatures: an egg shell is patterned with an MFP head levitating above the egg surface;

FIG. 5b is an enlarged view of a portion of FIG. 5a;

FIGS. 1-4, 6 and 7 are schematical, simplified representations, not necessarily at scale.

DETAILED DESCRIPTION

According to a first aspect, the present invention is embodied as a microfluidic surface processing system comprising: a microfluidic probe head, comprising a processing fluid circuit designed for dispensing a surface processing fluid from a processing fluid aperture thereof; a linkage mechanism, configured to apply a force to or modulate a force applied to the microfluidic probe head towards a surface to be processed; and a lifting fluid circuit, the circuit being: integral with the microfluidic probe head; distinct from the processing fluid circuit; and designed for dispensing a lifting fluid from a lifting fluid aperture thereof, with pressure such as to counter the force applied or modulated by the mechanism, at the level of the surface.

In embodiments, the mechanism is a rotatable device comprising a counterweight, the counterweight being adjustable, and wherein the microfluidic probe head is on one side of the rotatable device and counterbalanced by the counterweight on another side of the rotatable device.

The rotatable device is a pivoted device that comprises a pivot and a beam pivotable at the pivot, the microfluidic probe head being maintained at one side of the beam opposite to the counterweight with respect to the pivot, the pivot being rotatable with respect to a support in which it is anchored.

In exemplary embodiments, the microfluidic probe head is suspended from the one side of the rotatable device, via an axis.

The at least one processing fluid aperture is arranged with respect to the at least one lifting fluid aperture such that a surface processing fluid dispensed via the at least one processing fluid aperture can remain confined in a lifting liquid dispensed via the at least one lifting fluid aperture.

In embodiments, the processing fluid circuit further comprises at least two processing fluid apertures, respectively forming an outlet aperture and an inlet aperture, the outlet aperture and the inlet aperture dimensioned and positioned such as to allow for collecting via the inlet aperture liquid dispensed via the outlet aperture.

The lifting fluid circuit further comprises at least two, more specifically three or more lifting fluid apertures.

In exemplary embodiments, two lifting fluid apertures of the lifting fluid circuit are open on distinct faces of the probe head, the distinct faces being contiguous.

The mechanism is coupled to the microfluidic probe head to provide an effective weight for the probe head that is between 0.02 and 1 gram.

In embodiments, the lifting fluid circuit is configured to ensure an average gap of 1 to 50 micrometers between the probe head and a surface to be processed, in operation.

The lifting fluid circuit and/or the processing fluid circuit are configured to enable flow rates between 5 to 100 microliters per minute.

In exemplary embodiments, the average diameter of an apex of the probe head that comprises the processing fluid aperture for dispensing the processing fluid is between 0.5 and 10 mm$^2$, and more specifically between 1 and 3 mm$^2$.

An average diameter of a processing liquid aperture is between 20 and 100 micrometers, and more specifically between 40 and 60 micrometers.

In addition, an average diameter of a lifting liquid aperture may be between 40 and 200 micrometers, and more specifically between 50 and 100 micrometers.

According to another aspect, the invention is embodied as a method of operating a microfluidic surface processing system according to the above embodiments, the method comprising the steps of: dispensing a lifting fluid via the at least one lifting fluid aperture; letting the probe head undergo the force applied by or modulated by the mechanism to approach a surface to be processed, by dropping the probe head; and processing the surface with the probe head.

Devices, systems and methods embodying the present invention will now be described, by way of non-limiting examples, and in reference to the accompanying drawings.

The following description is structured as follows. First, general embodiments and high-level variants are described (sect. 1). The next section addresses more specific embodiments and technical implementation details (sect. 2).

1. General Embodiments and High-Level Variants

Referring generally to FIGS. 1 to 7, an aspect of the invention is first described, which concerns a microfluidic surface processing system 1.

System 1 basically comprises three elements, which are:
1. A MFP head 10;
2. A mechanism 40 to urge the MFP against the processed surface S; and
3. A lifting fluid circuit 30.

The MFP head 10 comprises a processing fluid circuit 20. The latter is designed for dispensing a processing fluid 25 which shall serve to process the surface S. This fluid is dispensed from an aperture 21 of the processing fluid circuit 20.

The mechanism 40 is a linkage mechanism, and in all cases is configured to apply a force to the MFP head towards the surface S, or to modulate a force (e.g., gravity) applied to the MFP head towards the surface S to be processed.

Finally, the lifting fluid circuit 30 is integral with the MFP head (e.g., provided directly within the MFP head or mounted onto, connected to the head, such as to be integral therewith). The lifting circuit is yet distinct from the processing fluid circuit. It is designed for dispensing a lifting fluid 35 (from an aperture 31 of the circuit 30), with pressure such as to counter the force applied or modulated by the mechanism 40, at the level of the surface S.

Thus, the underlying concept is twofold:

(1) The mechanism 40, e.g., a rotatable or pivoted system 40, interacts with the MFP head such that the latter is gently urged against the surface to be processed, i.e., the resulting force $F_w$ is small; this will be exemplified below.

(2) A fluid (typically a liquid) is dispensed from one or more apertures 31 of the lifting circuit 30 to generate a pressure at the head, e.g., underneath the head, thereby lifting it from the surface S. The resulting hydrodynamic lifting counterbalances the force $F_w$ that otherwise urges the probe head against the surface. This ensures a safe gap d, i.e., a minimal distance to the processed surface S (which most generally is not part of the invention, although it can be in embodiments).

The underlying principle can otherwise be regarded, at least in some cases, as a combination of short-range (repulsive) and long-range (attractive) forces that act onto the MFP head to let it self-regulate onto the processed surface S.

Altogether, the above system enables a simple self-regulated and automated distance control of the MFP head. Yet, no or few external control is required. A corresponding method of operation (which concerns another aspect of the present invention) is as follows. First, a lifting fluid is dispensed S1 via one or more apertures 31 of the lifting fluid circuit 30 (circuit 30 is switched "on"). Then, one lets S2-S4 the probe head 10 undergo the force applied by or modulated by mechanism 40, to approach a surface S to be processed (e.g., by simply dropping the probe head 10 above the surface). Finally, the surface S can be processed with the probe head 10, thanks to the processing circuit 20.

Figure 1:
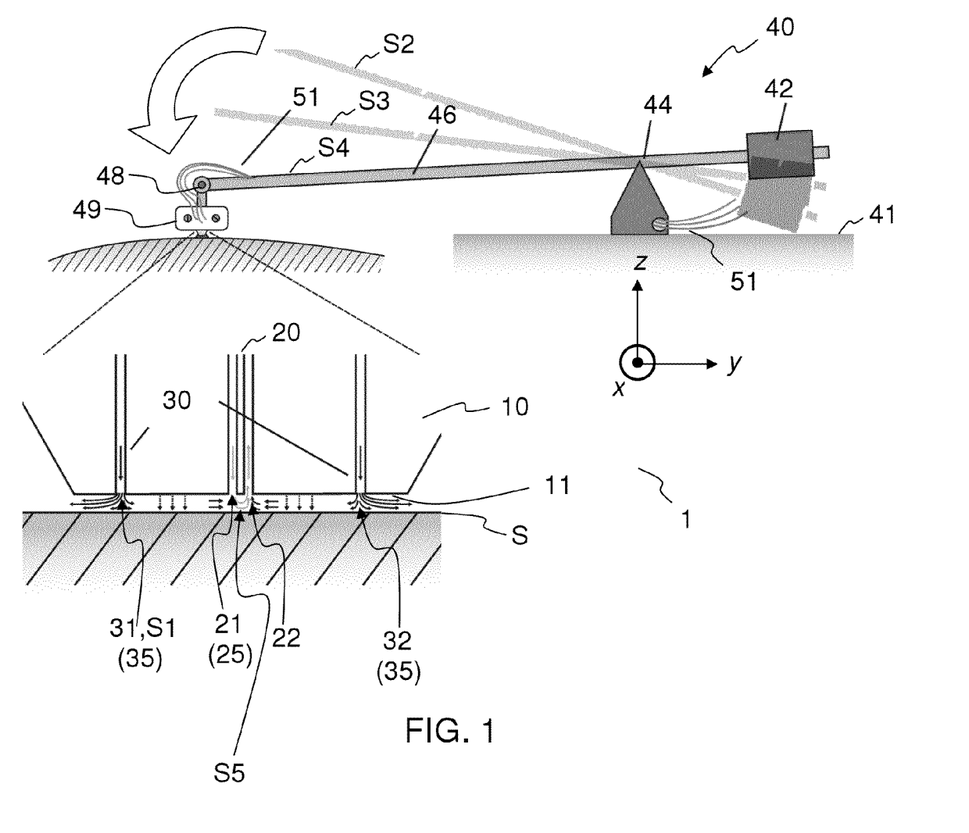
FIGS. 1, 6 and 7 are 2D views of a simplified representation of microfluidic surface processing systems with self-regulated distance control to the processed surface, according to embodiments of the invention.
Figure 6:
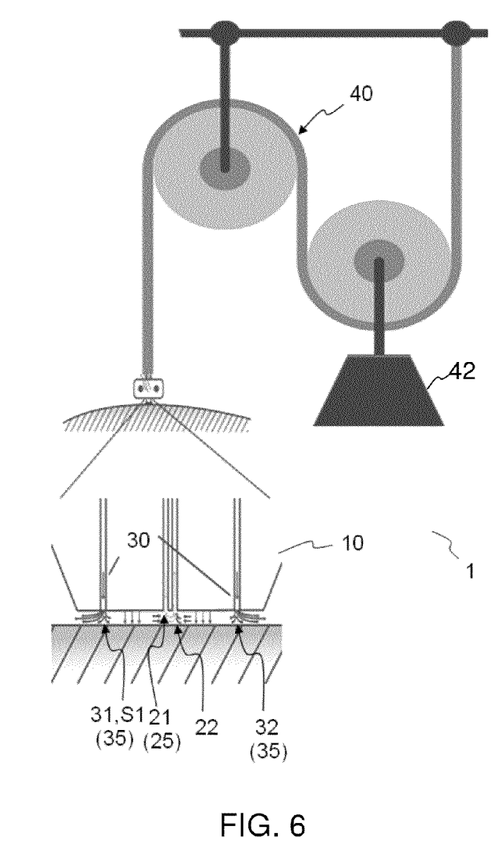
Figure 7:
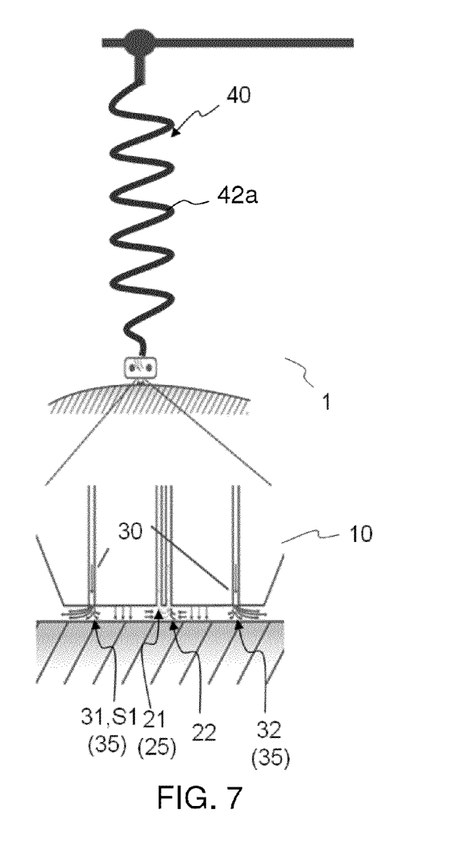

For example, in upside-down embodiments such as depicted in FIG. 1, 6 or 7, the mechanism 40 includes a counterweight 42 or a spring 42a to attenuate the gravity force acting on the head 10. Once the head is suitably weighted, e.g., counterbalanced by the counterweight, its effective weight becomes small. Still this effective weight results in urging the head against surface S. Finally, the lifting circuit 30 shall ensure a minimal approach distance d, such that it suffices to simply drop the head over the surface to position it onto the surface S to be processed (after the lifting circuit has been switched on. As a result, the head gently falls onto the surface, without damaging itself or the surface, a thing that visually is impressive. The operation of the MFP is accordingly radically simplified.

Note that if the probe head is operated upside-down (as illustrated in FIGS. 1, 6 and 7), opposite setups are possible in which an upward force is applied (instead of modulating gravity) to urge the head against the surface. Still, this upward force can still be countered by the lifting force $F_l$. In all cases, the lifting force $F_l$ is opposite to the urging force $F_w$, such as to counter it at the level of the processed surface. At the level of the surface, the apex of the head (exposed to the processed surface) oscillates around an equilibrium position, in operation. Yet, the urging force $F_w$ shall on average be equal (in magnitude) but opposite to the lifting force $F_l$.

Most embodiments described below, however, concern upside-down mechanisms, e.g., rotated or pivoted devices such as a balanced rocker arm, where the gravity force is attenuated but not completely countered by the urging mechanism 40. Such a mechanism confers a small effective weight to the head. This type of embodiments makes the operation of the system extremely easy.

For instance, and as illustrated in FIG. 1, 6 or 7, at steady state, the lifting height of the MFP head 10 notably depends on the configuration of the actual mechanism 40 used, e.g., a counterbalanced pivot (as in FIG. 1), a pulley/counterweight system (FIG. 6) or a spring (FIG. 7). Thus, the lifting height depends on the effective weight conferred to the head. This lifting height shall further depend on the flow rates set at the apertures 31, 32 of the lifting fluid circuit 30, the type of fluid used, as well as the area of the MFP exposed to the surface to be processed, i.e., the area of the apex 11 of the MFP head. Fine tuning of these parameters can be achieved by trials and errors, thanks to standard equipment used in MFP technologies, e.g., pumps, microchannels within the MFP head, yet dedicated in the present context to the purpose of creating a suitable lifting force $F_l$, to counter the urging force $F_w$.

An interesting and fortunate advantage of systems such as described above is that when the MFP head 10 encounters a (typical) topographical variation on a (typically) processed surface S, the distance to the surface automatically self-corrects.

Another positive side-effect is that no dust particles can enter the gap, provided that the lifting circuit 30 is suitably arranged at the head, e.g., surrounds it or, better, is configured directly within the MFP head, e.g., in the same way as the processing liquid circuit 20 is. The processing fluid 25 can even be confined in the lifting fluid 35. In that case the fluids 25, 35 both are liquids. The lifting liquid 35 can therefore also serve as immersion liquid in that case, provided that additional features are present, which are discussed in detail below. However, an immersion fluid circuit could also be provided separate from both the lifting fluid circuit and the processing liquid circuit.

In this respect, most embodiments shall typically make use of liquids, although specific applications may use gas instead of liquid, be it in the lifting circuit and/or in the processing circuit. In addition, liquids with different viscosities could be used, e.g., to increase the lifting effect.

As touched earlier, the mechanism 40 used to urge the MFP head 10 against the surface S can take several forms. Essentially two limit classes of embodiments can be distinguished, as evoked above. In the first case, this mechanism 40 partly counterbalances gravity in order to confer a low effective weight to the head (upside-down setups). In the second case, the mechanism overcomes gravity to gently urge the head against a surface to be processed (inverted setups). Of course, several mixed or intermediate types of embodiments can be contemplated between these two limit cases. Still, in all cases mechanism 40 interacts with the head such as to exert a reasonably small pressure to the head, towards the surface. Thus, one understands that the mechanism 40 may be embodied in various manners. The appended drawings illustrate possible variants. A first class of variants concerns rotated systems: suitable rotated devices notably include: pivoted devices (beam or lever, FIG. 1), a balance, rope and pulley systems (block and tackle, FIG. 6). Another class of variants makes use of springs, e.g., spring-retained systems (as illustrated in FIG. 7). Not all variants are illustrated, for the sake of conciseness. Still, other variants may rely on a compressed spring, air suspension, electrostatic or magnetic devices, etc., as many systems which are capable of applying or modulating a force applied to the MFP head. Still, the hydraulic pressure that otherwise results from the lifting circuit 30 can be jointly designed to compensate the small weight autonomous.

The lifting fluid circuit 30 is integral with the MFP head e.g., combined, combinable with or connectable to the head 10 in order to achieve the desired effect, i.e., that a lifting fluid 35 be dispensed with pressure such as to counter the long-range force $F_w$. The long-range force $F_w$ is countered at the level of the surface S, subject to the minimal approach distance d evoked earlier. The lifting fluid 35 does not necessarily have to come out of the MFP head 10 itself, i.e., the lifting fluid circuit, needs not necessarily be integrated within the head, although it is desirable, be it for ergonomics or for reasons mentioned earlier. Still, the lifting fluid 35 could also be dispensed from a separate holder, a small chip or a device nearby, a packaging around the chip, etc., any device integral with the head 10.

Two embodiments of the invention are now discussed in more detail.

As evoked earlier, the mechanism is a rotatable device 40 equipped with a counterweight 42, as illustrated in FIGS. 1 and 6. The MFP head is located on one side of the rotatable device 40 and counterbalanced by the counterweight 42 located on the other side. The effective weight of the head 10 is in that case simply modulated, i.e., counterbalanced thanks to the counterweight 42.

In the embodiment of FIG. 1, the rotatable device 40 is a pivoted device that comprises a pivot 44 and a beam (i.e., a lever) 46, the latter pivotable at the pivot 44. The MFP head 10 is maintained at one side of the beam 46, opposite to the counterweight 42, with respect to the pivot 44. The pivot is rotatable with respect to a support 41 in which it is otherwise anchored. Using a pivoted system (like the pivot of FIG. 1 or any similar balance-type systems allows for more easily handling the MFP head, compared with a rope and pulley system such as depicted in FIG. 6 or a spring-based system (FIG. 7). All the more, an adjustable counterweight 42 can more easily be integrated a pivoted system, as illustrated in FIG. 1. The pivot 44 enables rotation of the beam 46 about at least one axis, or still, two or, even, three axes if necessary. In this example of FIG. 1, the MFP head is mounted at one end of the beam. Pivoting the beam (with respect to x-axis) allows for two limit positions, respectively corresponding to (i) a surface processing state (lower position of the head), where the head's apex 11 is close to the surface S and (ii) a non processing state (upper position). Still, the pivot 44 can possibly be rotatable parallel to the support 41 (with respect to z-axis) in which it is otherwise anchored, like in a phonograph turntable configuration. This additional rotation axis allows for improved ergonomics, e.g., the surface S can be left in position while bringing the head back and forth from the processing location, at no risk for the surface. In the remote position, the head can be mounted (e.g., suspended), inspected, cleaned, etc., remote from the surface sample. The pivot could also be slidably mounted or, still, rotatable and slidable with respect to the support 41.

In other words, in embodiments, the user can operate such a delicate thing as a MFP head similarly as a phonograph turntable stylus, except that the MFP head can be handled in an even ruder manner. Indeed, the lifting fluid pressure shall ensure a soft landing of the head 10. The small effective weight of the head slightly overcomes the friction at the main rotation axis x, such that the head shall gently fall onto the surface S. In practice, it suffices to simply drop the head over the surface after the lifting circuit has been switched on. In this respect, the mechanism 40 is designed to provide an effective weight $F_w$ to the probe head that is between 0.02 and 1 gram. This range is what appears to be the best suited in practice, resulting in no damage for the surface S or for the head 10.

In this regard, an adjustable counterweight system 42 is used, for fine-tuning the effective weight of the head. This adjustable counterweight can for instance simply consist of a slidable weight mounted opposite to the head. Other adjusting systems can be contemplated, such as known per se in balances or weighing scales e.g., a cursor is set at the level of the pivot. Thus, the adjustable counterweight mechanism can be partly independent from the counterweight 42 depicted in FIG. 1. Several counterweights could further be contemplated for coarse and fine tuning. In all cases, an adjustable counterweight allows for easily tuning the effective weight of the MFP head. An optimal weight adjustment requires ~10 mg precision in practice, as present inventors concluded.

The MFP head is suspended from one side of the beam 46, via an axis 48. A holder 49 can further be provided for the purpose of fixing, weight distribution, etc., to the MFP head upper part. Suspending the MFP head ensures that the head shall remain vertical, i.e., the flow direction remains perpendicular to the sample surface S. Such a design is furthermore less encumbering compared to designs where the head is maintained at one end of the beam.

Referring to FIGS. 1-4 altogether: a processing fluid aperture 21 may be arranged with respect to a lifting fluid aperture 31 such that a surface processing fluid 25 dispensed via the processing fluid aperture 21 can remain confined in the lifting liquid 35. Indeed, as evoked earlier, the lifting liquid 35 can serve as immersion liquid too, which allows to save one fluid circuit. How to confine a processing liquid within an immersion liquid and the related technical advantages are otherwise known per se in MFP technology.

The processing fluid circuit 20 typically comprises two processing fluid apertures 21, 22 (or more if needed), respectively forming an outlet aperture 21 and an inlet aperture 22. The outlet 21 and the inlet 22 are dimensioned and positioned such as to allow for collecting via the inlet 22 some fluid that is dispensed via the outlet 21. In the present context, the average diameter of the outlet and the inlet may advantageously be design to be between 0.5 and 1000 micrometers (at the level of the apex 11). The outlet may for instance be designed small enough to enable a local liquid confinement, if needed. Such a confinement (of e.g., 150 micrometers) is best obtained with outlets of about 20 to 50 micrometers. It can yet be fabricated substantially smaller, e.g., 0.5 micrometers, which may be useful in some specific applications. The apertures 21, 22 end, each, a respective outlet/inlet conduit having the same diameter as the corresponding aperture 21, 22. Yet, the sizes of the inlet and outlet may substantially differ, e.g., small outlet, large inlet. The inlet aperture 21 indeed is in some cases much larger than the expected confinement size, especially where one seeks to prevent clogging by particles/dust. The dimensions retained for the apertures and their asymmetry strongly depends on the application sought. The flow characteristics enabled by the indicative dimensions given above are suited for a range of applications. For completeness, the distance between the outlet aperture 21 and the inlet aperture 22 is typically more than 5 micrometers, but also less than 2000 micrometers. With such dimensions, a stable confinement can in principle be achieved. Smaller dimensions are impractical in terms of fabrication, while larger dimensions may result in an unstable confinement. Laminar liquid flows may be desired.

Figure 2:
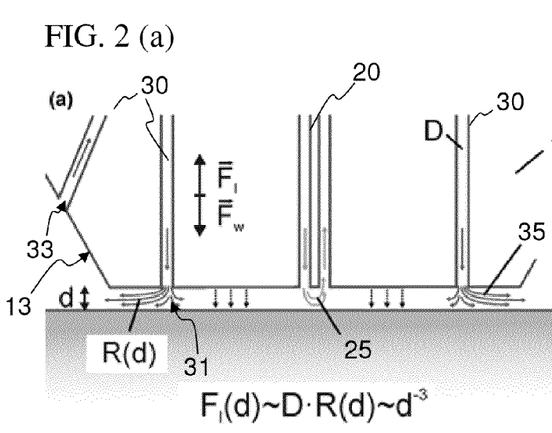
FIGS. 2(a)-(c) focus on a microfluidic probe head (or MFP head) that can be used in systems according to the invention, and its interaction with a surface processed by the head.
Figure 3:
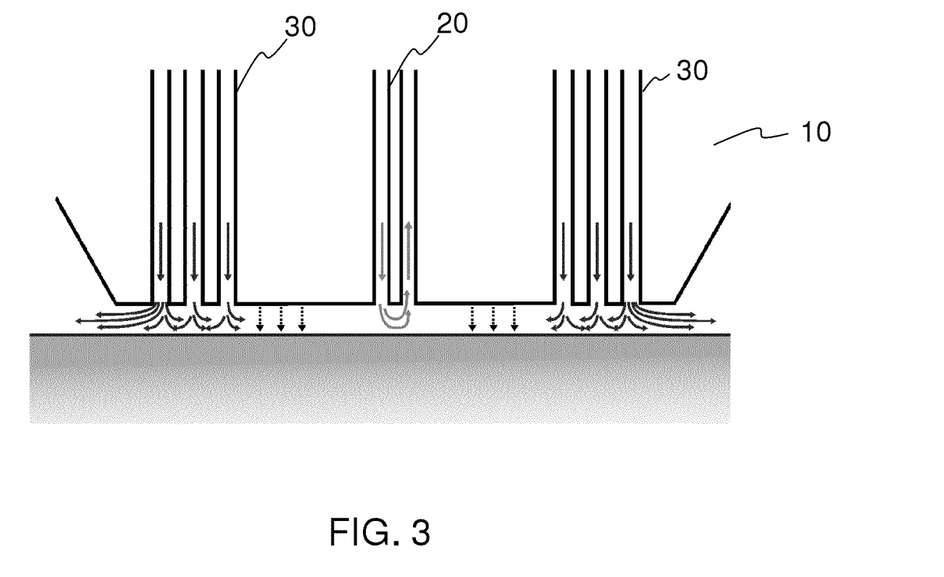
FIG. 3 depicts a variant to FIG. 2(a)
Figure 4:
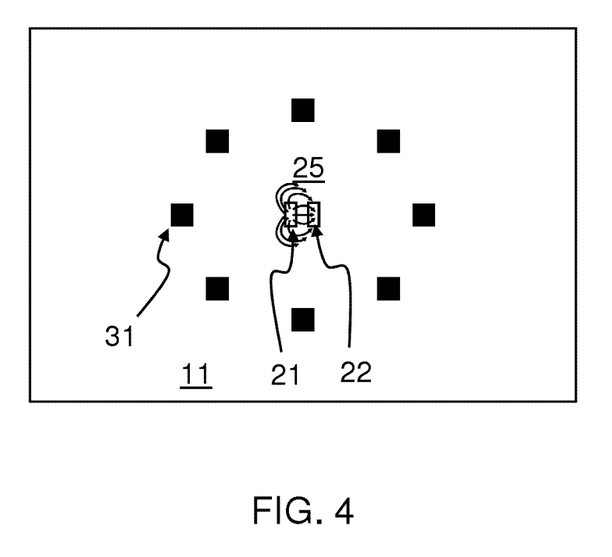
FIG. 4 depicts a variant to FIG. 2(c)

Referring now to FIGS. 2-4: in embodiments, the lifting fluid circuit 30 may further comprise two, more specifically three or more apertures 31, 32, 33. In particular, referring to FIGS. 2(*a*) and 2(*b*), two lifting fluid apertures 31, 33 of the lifting fluid circuit 30 may advantageously be open on distinct faces 11, 13 of the probe head 10. The distinct faces 11, 13 are yet typically contiguous, as illustrated in FIG. 2(*a*). Indeed, as present inventors have realized, a build-up of liquid at the apex 11 of the MFP head may in some cases impact the levitation of the head. Although this issue does not systematically occur (this notably depends on the lifting liquid used), this phenomenon can for instance be dealt with by re-adjusting the counterweight 42. By providing additional microchannels and corresponding apertures 33 on the edge 13 of the head, excess liquid can more easily be removed, and this, continuously, without requiring any counterweight re-adjustment. The additional microchannels and corresponding apertures 33 may form part of a circuit (dedicated to excess liquid removal) independent from the basis lifting circuit 30, as exemplified in the embodiment of FIG. 2(*b*).

The dimensions of the additional aperture 33 and the corresponding conduits/microchannels can be the same as for the outlet/inlet apertures/conduits 31, 32. Thus, additional channels can be provided on the side of the MFP head to pull away the excess lifting liquid. For instance, as depicted in FIG. 2(*a*) or (*b*), one such channel can be provided on each side 13 of the chip, contiguous with the apex 11. For completeness, FIG. 2(*b*) is a photograph of a MFP head comprising distinct fluid circuits 20, 30, 33, here respectively dedicated to flow confinement, levitation, and aspiration of excess liquid/immersion liquid. These circuits include conduits or microchannels, corresponding apertures and vias like via 33*v* ending the circuit of the outer fluid removal circuit 33. The vias enable fluid communication from/to other components of the microfluidic probe device (not shown).

As touched earlier, the precise configuration of the lifting fluid circuit 30 depends on a number of parameters. Still, it is configured to ensure an average gap d between the probe head's apex and the surface, which gap on average is comprised between 1 and 50 micrometers. Indications as to the relative dimensions are given in FIG. 2(*a*): a lifting force $F_l$ acts on the MFP head due to a liquid flow (D) through the levitation apertures 31, 32, resulting in a lifting height d (assuming laminar flow). The lifting force $F_l$ is proportional to D·R(d), which turns out to be approximately proportional to $d^{-3}$, where R denotes the hydrodynamic resistance and D is the volumetric flow rate of the liquid (as can be derived from basic physical laws, in particular Navier Stokes equation, applied to the present context).

In typical embodiments, the lifting fluid circuit 30 and/or the processing fluid circuit 20 are configured to enable flow rates between 5 to 100 microliters per minute. Various types of processing liquids are used, as known per se. The lifting fluid can be liquid, and chosen amongst organic solvents or ionic liquids. Gases can be used as well, e.g., air.

In one exemplary embodiment, a MFP head (made of silicon/glass) is used, which comprises additional etched microchannels for levitation liquid, as in FIG. 2(b). This MFP head is connected to external pumps; flow rates are on the order of 5-100 µL per minute; the weight adjustment is achieved with a rocker arm (equipped with a counterweight that provides ~10 mg precision); the weight of the head after adjustment is ~0.02-1 gram and the gap to the substrate that can be achieved is typically of 1-50 µm, with a levitation liquid being an aqueous solution.

FIG. 2(c) is a representation of typical flow lines between apertures 31, 32 and 21, 22, modeled from observations, notably microscope images of a confinement of a fluorescein solution (the levitation and processing liquid are miscible in this example). The smallest arrows show the confinement of processing liquid 25, the largest arrows represent the liquid injected through the levitation apertures 31, 32. In this example, the dimensions and flow velocities of the levitation liquids 35 do not disrupt the laminar flows within the processing liquid 25.

The average diameter of the apex 11 of the probe head is typically between 0.5 and 10 mm$^2$, and more specifically between 1 and 3 mm$^2$. In addition, the average diameter of processing liquid apertures is typically between 20 and 100 micrometers, and more specifically between 40 and 60 micrometers. The average diameter of lifting liquid apertures is typically between 40 and 200 micrometers, and more specifically between 50 and 100 micrometers. The above dimension ranges have proved to be well suited for a range of surface processing applications that present inventors have explored.

For example, the embodiment of FIG. 2(c) has the following set of specifications: which proved useful in practice:

Apex size: 1 mm×1.5 mm;
Aperture size for flow confinement: ~50 µm
Aperture size for levitation: 50-100 µm (with two apertures per MFP head), i.e., apertures 31, 32 are typically larger than apertures 21, 22;

Note that in FIG. 2(c), no aperture is provided to withdraw the levitation liquid, as opposed to FIGS. 2(a) and (b).

Next, in the embodiment of FIG. 3, multiple parallel injection conduits and corresponding apertures are implemented for dispensing the levitation/immersion liquid, a configuration which can serve to tune the performance of the lifting. Different flow rates can for instance be provided in each injection conduit, if necessary (lifting fluid apertures can be individually addressed to adjust the parallelism of the head to the substrate). One benefit is to gain an efficient lifting force without disturbing the flow confinement of the processing liquid. In FIG. 4, multiple injection apertures for the levitation liquid are implemented, symmetrically arranged around the processing liquid apertures 21, 22. This configuration also helps in improving the performance of the lifting. Yet the configuration of the lifting fluid apertures in FIG. 4 requires using a horizontal MFP chip, as opposed to the parallel configuration of FIG. 3, which is compatible with a vertical MPF probe head such as depicted in FIG. 2(a). Finally, it is noted that large flow resistance could be advantageously used for better lifting performance, because the lifting force scales linearly with the resistance, $F_l$~R. Obviously, more complicated (yet optimized) aperture geometries can be contemplated.

FIGS. 5(a) and 5(b) are a photograph of a setup for local staining of a surface with large curvatures. As a prototype, an egg shell S is patterned with the levitating MFP head 10. This setup consists of a motorized stage 60, a MFP head 10 clamped in a holder 49, which was mounted on a rocker arm 46 to balance the weight of the MFP head. The close-up shows the holder 49 with the levitating MFP head 10 interacting with the egg shell S. An egg was chosen as a particularly challenging surface, as indeed it has a non planar, non regular topography. The photographs otherwise show tubings 51 and sample skewer 52. Other referenced components correspond to those already discussed in respect of FIG. 1.

Figure 5:
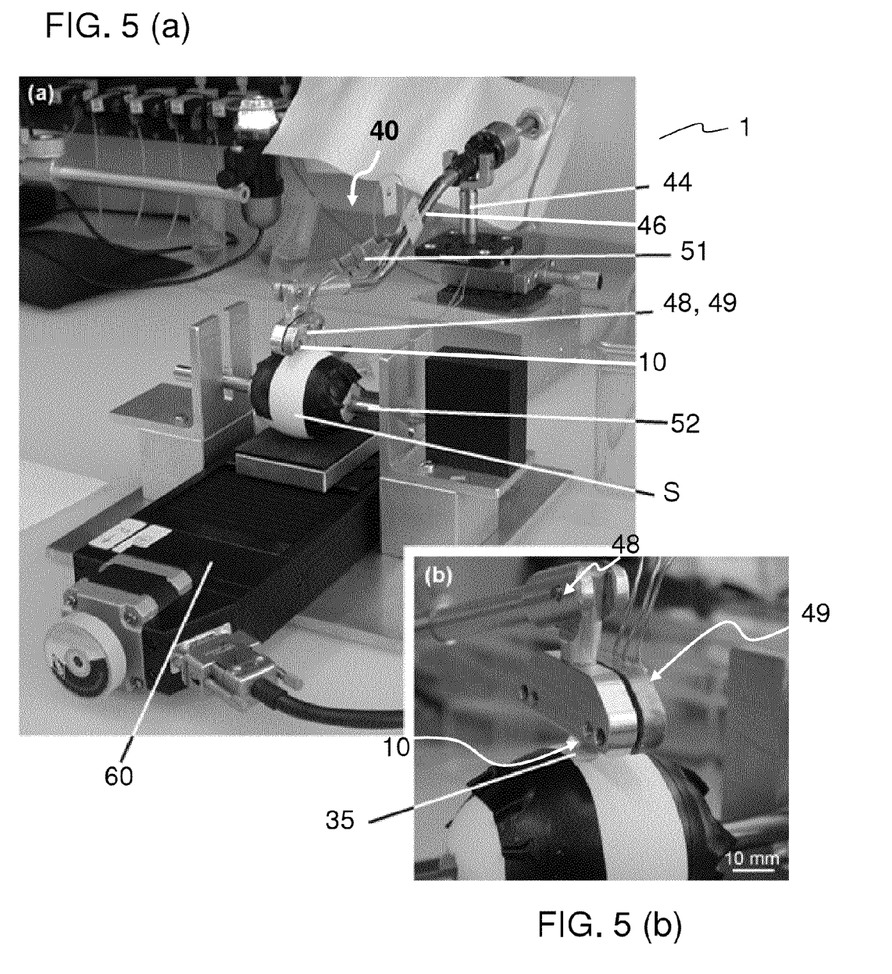

The setup of FIG. 5 was used, as a test, to draw lines of 75 to 100 µm width with logwood brew on the shell of the egg. In addition, present inventors have tested various setups according to this invention for the local processing of other "challenging" surfaces. For example: a 35-µm-thick Cu surface was locally etched using a confined $Na_2S_2O_8$ solution (20% w/v). Some of the setups were tested for etching and interacting with non-transparent substrates. Concerning bio-applications, systems according to this invention can be used for staining tissue sections (immunohistochemistry, fluorescence in situ hybridization, RNA extraction), as present inventors have tested.

The above embodiments have been succinctly described in reference to the accompanying drawings and may accommodate a number of variants. For example: spacing between the levitation apertures can be varied; different geometries could be provided to the levitation apertures; other materials could be used to fabricate the MFP head (glass, silicon, polymers, metals, etc.); the size of the device/chip may vary from a few millimeters to several centimeters; the apex of the MFP head does not have to be flat. It could be slightly concave or still be provided with a cavity for modulating/improving the lifting performance; and finally, the weight adjustment could be realized with other mechanisms, e.g. magnetic lifting. Several combinations of the above features may otherwise be contemplated. Examples are given in the next section.

2. Specific Embodiments/Technical Implementation Details

Exemplary embodiments basically make use of a multilayered MFP head. As in microfluidic devices in general, the present surface processing devices may be equipped with user chip interfaces and closed flow paths. Closed flow paths facilitate the integration of functional elements (e.g. heaters, mixers, pumps, UV detector, valves, etc.), which may be integrated to present surface processing devices, while minimizing problems related to leaks and evaporation.

MFP heads are fabricated as a multilayer device, to ease the fabrication of inner microchannels (as visible in FIG. 2(b)). Such MFP heads can be microfabricated using Si wafers, although other materials can be used. For example, an upper layer (Si), i.e., a Si lid may be provided on top of a HFC chip. A single-side and a double-side polished Si wafer may be used for the Si and HFC chip, respectively. Both wafers are e.g. 4 inch in diameter and 400 µm in thickness (Siltronix, Geneva, Switzerland). The microstructures can be made using standard photolithography, photoplotted polymer masks (Zitzmann GmbH, Eching, Germany) and DRIE, see e.g. STS ICP, Surface Technology Systems, Newport, UK. The microchannels of the HFC chips can be etched 50 µm deep into the upper face of the HFC wafer. The bottom side of the wafer can be processed to form mesas and posts, if necessary, to a height of 50 µm. Opening the apertures can be performed using DRIE etching from the bottom side of the HFC wafer. Well defined apertures with lateral dimensions of less than 10 µm can thereby be obtained. The apertures can be more accurately fabricated when a thin Si wafer is used for the HFC chip while the lid wafer can remain thick to provide mechanical strength to the head.

The Si lid can be produced by etching vias with a diameter of 800 µm trough a one side polished wafer. Next, assembly of both wafers is achieved by spin coating ~3 µm of a polyimide adhesive (HD Microsystems GmbH, Neu-Isenburg, Germany) onto the polished side of the lid wafer and by subsequently aligning and bonding both wafers. Bonding take place at 320° C. with 2 bar pressure for 10 minutes (PRESSYS LE, Paul-Otto Weber GmbH, Remshalden, Germany). The upper lid can be terminated with any appropriate layer for enabling sensing, if necessary. The MFP heads can then be diced and stored. Mounting the ports can be carried out using epoxy adhesive rings (Nanoport™ Assemblies from Upchurch Scientific, Ercatech, Bern, Switzerland, epoxy adhesive rings are supplied). The use of standard ports and fittings in place of e.g. molded block of PDMS diminishes labor needed for assembling a head. MFP heads are tested for leakage and clogging before actually mounting the ports, as incursion of adhesive into the microchannels cannot be excluded. In that respect, a disposable pipette tip can be cut to match the size of the vias and liquid can be pushed through the channels while observing with a magnifying glass if droplets are able to exit the apertures without leaking elsewhere. Alignment of the ports with the vias can finally be done manually. A subsequent bonding take place, e.g. at 140° C. for ~1 hour on a hotplate or in an oven.

Incidentally, multilayered heads such as discussed above are also more amenable to using many liquids because apertures can be small and close to each other with horizontal microchannels sufficiently fanning out for leaving sufficient space for adding many ports on the Si lid.

Finally, typical requirements (for typical applications of the present embodiments) are now discussed, which notably concern: lateral displacement during scanning, scanning speed, response time, liquid volumes, footprint, etc.

1. Lateral Displacement During Scanning (Travel Range)

Systems such as described above will be used on glass slides (typically 25 mm×75 mm). Yet, given the linear drives (stages) that are currently available, surfaces up to 10 cm×10 cm can be scanned. The example of FIG. 5 shows that also a continuous movement in one direction is possible.

2. Scanning Speed

Surface processing can be performed stationary, or not. For instance, the scanning speed can be varied from about 0.1 micrometer per second up to millimeters per second. For example, if one wants to loose contact between the processing solution and the surface, then the scanning speed may be increased to, e.g., 5 mm per second. The levitation effect still works at this speed but no patterning is anymore possible. Thus, sudden speed variation can be used to make discontinuous patterns (stop and go movement). Scanning speeds between 0.1 µm/s to 100 µm/s are otherwise used for continuous patterning.

3. Response Time

The response time in sufficiently adapting the distance to the surface topography is normally in the sub-second regime (<1 s), and should likely remain above 1 microsecond.

4. Volumes, Laminar Flow, Stability

As touched earlier, advantage can be taken of scaling, so as to benefit from physical phenomena of laminar flows. Due to laminar flows, a high stability can be achieved when the balancing of the MFP head reaches equilibrium. Without any external disturbance, the MFP head remains surprisingly stable above the surface (typically within less than a few micrometers in the direction of application, i.e., z-direction in FIG. 1), especially when the head is applied with an effective force $F_w$ between 0.02 and 1 gram. Furthermore, the flow confinement of the processing liquid is not distorted, a thing that is not possible with turbulent flows.

5. Localization and Footprint

Another remarkable aspect of at least some of the embodiments discussed earlier is that one can process (e.g., stain) locally with a certain footprint (typically 150 µm×75 µm for the MFP). In embodiments where excess levitation fluid is aspirated, it is possible to reduce the total liquid footprint of the system (processing liquid plus levitation liquid), and this, up to ~10 times of the size of the processing fluid footprint (but typically ~5 times). In some cases, where the surface is sensitive to liquid, one would like to have the total footprint as small as possible. In other examples it does not matter as long as the levitation liquid does not start to pull down the head.

To conclude, distance regulation of microfluidic surface processing devices is a key aspect for microfluidic probe technology. The methods and devices described here work for a range of viscosities, geometries and topographies. While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other mechanisms can be used to modulate gravity or apply a convenient force to the MFP head toward the surface. Also, a MFP head could be suspended from the beam via a spring, etc., to better accommodate topological variations of the processed surface.

REFERENCE LIST

1 Microfluidic Surface Processing System
10 Microfluidic Probe Head
11 MFP Head Apex
13 Contiguous Face (Contiguous to the Apex)
20 Processing Fluid Circuit
21, 22 Processing Fluid Apertures
25 Surface Processing Fluid
30 Levitation Fluid Circuit
31, 32 Levitation Apertures
33 Levitation Liquid Withdrawal Apertures/corresponding Circuit
33v Liquid Withdrawal Circuit Via
35 Levitation Liquid
S Processed Surface
40 Urging Mechanism (Rotatable, Pivoted Device, etc.)
41 Pivot Support
42 Counterweight
42a Spring
44 Pivot
46 Beam
48 Suspension Axis
49 Suspension Holder
51 Tubings
52 Sample Skewer
60 Motorized Stage
d Gap To The Surface (m)

D Volumetric Flow Rate ($m^3/s$)
$F_l$ Lifting Force (N)
$F_w$ Urging Force (Gravity) (N)
R Hydrodynamic Resistance ($1/m^3$)

The invention claimed is:

1. A method of operating a microfluidic surface processing system having a microfluidic probe head having a processing fluid circuit configured to dispense a surface processing fluid from a processing fluid aperture thereof, a linkage mechanism, configured to apply a force to or modulate a force applied to the microfluidic probe head towards a surface to be processed, and a lifting fluid circuit integral with the microfluidic probe head and distinct from the processing fluid circuit, the lifting fluid circuit designed for dispensing a lifting fluid from a lifting fluid aperture thereof, with pressure such as to counter the force applied or modulated by the linkage mechanism, at the level of the surface, the method comprising:

dispensing a lifting fluid via the at least one lifting fluid aperture;

letting the probe head undergo the force applied by or modulated by the mechanism to approach a surface to be processed, by dropping the probe head; and processing the surface with the probe head.

2. The method of claim 1, wherein the linkage mechanism is a rotatable device comprising a counterweight, the counterweight being adjustable, and wherein the microfluidic probe head is on one side of the rotatable device and counterbalanced by the counterweight on another side of the rotatable device.

3. The method of claim 2, wherein the rotatable device is a pivoted device that comprises a pivot and a beam pivotable at the pivot, the microfluidic probe head being maintained at one side of the beam opposite to the counterweight with respect to the pivot, the pivot being rotatable with respect to a support in which it is anchored.

4. The method of claim 3, wherein the microfluidic probe head is suspended from the one side of the rotatable device, via an axis.

5. The method of claim 1, wherein the at least one processing fluid aperture is arranged with respect to the at least one lifting fluid aperture such that a surface processing fluid dispensed via the at least one processing fluid aperture can remain confined in a lifting liquid dispensed via the at least one lifting fluid aperture.

6. The method of claim 1, wherein the processing fluid circuit further comprises at least two processing fluid apertures, respectively forming an outlet aperture and an inlet aperture, the outlet aperture and the inlet aperture dimensioned and positioned such as to allow for collecting via the inlet aperture liquid dispensed via the outlet aperture.

* * * * *